(12) United States Patent
Hougland (10) Patent No.: US 9,340,578 B2
(45) Date of Patent: May 17, 2016

(54) INHIBITORS TARGETING HUMAN GHRELIN O-ACYLTRANSFERASE

(71) Applicant: James Hougland, Fayetteville, NY (US)

(72) Inventor: James Hougland, Fayetteville, NY (US)

(73) Assignee: SYRACUSE UNIVERSITY, Syracuse, NY (US)

( * ) Notice: Subject to any disclaimer, the term of this patent is extended or adjusted under 35 U.S.C. 154(b) by 125 days.

(21) Appl. No.: 14/328,800

(22) Filed: Jul. 11, 2014

(65) Prior Publication Data

US 2015/0018520 A1    Jan. 15, 2015

Related U.S. Application Data

(60) Provisional application No. 61/846,235, filed on Jul. 15, 2013.

(51) Int. Cl.
*C07K 7/06* (2006.01)
*C12N 9/10* (2006.01)

(52) U.S. Cl.
CPC ............... *C07K 7/06* (2013.01); *C12N 9/1029* (2013.01)

(58) Field of Classification Search
CPC .............. A61K 31/4196; A61K 31/41; A61K 31/4192; A61K 38/00; C07D 249/08; C07D 249/04; C07D 249/14; C07D 413/06; C07K 7/08; C07K 16/2863; C07K 7/06
See application file for complete search history.

(56) References Cited

U.S. PATENT DOCUMENTS 6,967,237 B2 * 11/2005 Bednarek ............... A61K 38/25 530/300
2007/0208061 A2 * 9/2007 Perrissoud ......... A61K 31/4196 514/341

FOREIGN PATENT DOCUMENTS

FR   WO 2007020013 A2 * 2/2007 ......... A61K 31/4196
FR          2431035 A1 * 3/2012 ......... A61K 31/4196
WO  WO 2010151675 A1 * 12/2010 ............... C07K 7/06

OTHER PUBLICATIONS

Kharb et al., Pharmacological significance of triazole scaffold, J. of Enzyme Inhibition and Medicinal Chemistry, vol. 26(1):1-21 (2011).*
Moulin et al., Toward Potent Ghrelin Receptor Ligands Based on Trisubstituted 1,2,4-Triazole Structure, J. Med. Chem., vol. 50:6790-5806 (2007).*
Baccile et al., Modular synthesis of photocleavable peptides using click chemistry, Tetrahedron Letters, vol. 53:1933-1935 (Feb. 9, 2012).*
Zhou et al., Recent Researches in Triazole Compounds as Medicinal Drugs, Current Medicinal Chemistry, vol. 19:239-280 (2012).*
Brett J.W. Teubner, et al, Inhibition of ghrelin O-acyltransferase attenuates food deprivation-induced increases in ingestive behavior, Hormanes and Behavior, (2013), http://dx.doi.org/10.1015/j.yhbeh.2013.02.001.

(Continued)

*Primary Examiner* — Maury Audet
*Assistant Examiner* — Randall L Beane
(74) *Attorney, Agent, or Firm* — Bond Schoeneck & King, PLLC; David Nocilly; George McGuire (57) ABSTRACT

Grhelin O-acyltransferase inhibitors using a triazole linkage to incorporate aromatic and alkyl substituents to mimic the natural octanoyl group attached to ghrelin. Inhibitors include a triazole portion, an alkyl linker, and a hydrophobic aromatic group on a side chain. The hydrophobic aromatic group may include various length alkyl linkers.

2 Claims, 6 Drawing Sheets n=1 inhibitor 6a
n=2 inhibitor 6b
n=3 inhibitor 6c

(56) References Cited

OTHER PUBLICATIONS

Hideko Ohgusu, et al., Ghrelin O-acyltransferase (GOAT) has a preference for n-hexanoly-CoA over n-octanoyl-CoA as an acyl donor, Biochemical and Biophysical Research Communications, 386 (2009) 153-158, journal homepage: www.elsevier.com/locate/ybbrc.

Amanda L. Garner, et al. A small molecule antagonist of ghrelin O-acyltransferase (GOAT), Chem Comm. 2011, 7512-7514, www.rsc.org/chemcomm.

Amanda L. Garner, et al., cat-ELCCA: A Robust Method to Monitor the Fatty Acid Acyltransferase Activity of Ghrelin O-Acyltransferase (GOAT), 2010 Wlley-VCH Verlag GmbH & Co. KGaA, Weinheim, Angew. Chem. Int. Ed. 2010, 49, 9630-9634.

Brad P. Barnett, et al., Glucose and Weight Control in Mice with a Designed Ghrelin O-Acyltransferase Inhibitor, Science, Dec. 17, 2010; 330 (6011): 1689-1692. doi: 10.1126/science.1196154.

Jing Yang, et al., Inhibitioin of ghrelin O-acyltransferase (GOAT) by octanoylated pentapeptides, PNAS/Aug. 5, 2008, 10750-10755, vol. 105, No. 31, www.pnas.org/cgi/doi/10.1073/pnas.0805353105.

* cited by examiner n = 1, 2, 3 n=1 inhibitor 6a
n=2 inhibitor 6b
n=3 inhibitor 6c

INHIBITORS TARGETING HUMAN GHRELIN O-ACYLTRANSFERASE

CROSS-REFERENCE TO RELATED APPLICATIONS

The present application claims priority to U.S. Provisional Application No. 61/846,235, filed on Jul. 15, 2014.

BACKGROUND OF THE INVENTION

1. Field of the Invention

The present invention relates to grhelin O-acyltransferase inhibitors and, more specifically, a small molecule peptidomimetic inhibitor targeting ghrelin O-acyltransferase.

2. Description of the Related Art

Ghrelin is a peptide hormone involved in appetite stimulation, regulation of glucose homeostasis, and a range of other physiological processes. Ghrelin requires a unique posttranslational modification, octanoylation of a serine side chain, to bind its cognate receptor and activate signaling. The enzyme that catalyzes this modification, ghrelin O-acyltransferase (GOAT), is receiving increased interest as a potential drug target for treatment of obesity, diabetes, and other diseases potentially linked to ghrelin signaling. As ghrelin is the only known substrate of GOAT, blocking ghrelin acylation using GOAT inhibitors potentially offers a specific and targeted avenue to treat diabetes, obesity, and other health conditions impacted by ghrelin signaling. Generating hGOAT inhibitors presents a significant challenge, however, due to the complete lack of structural information and minimal mechanistic information available regarding hGOAT. As a result, very little rational drug design can be carried out.

BRIEF SUMMARY OF THE INVENTION

The present invention comprises a synthetic grhelin O-acyltransferase inhibitor having a triazole portion, an alkyl linker, and at least one hydrophobic aromatic group on a side chain. The hydrophobic aromatic group may comprise multiple aromatic groups. The inhibitors of the present invention use a triazole linkage to incorporate aromatic and alkyl substituents to mimic the natural octanoyl group attached to ghrelin.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
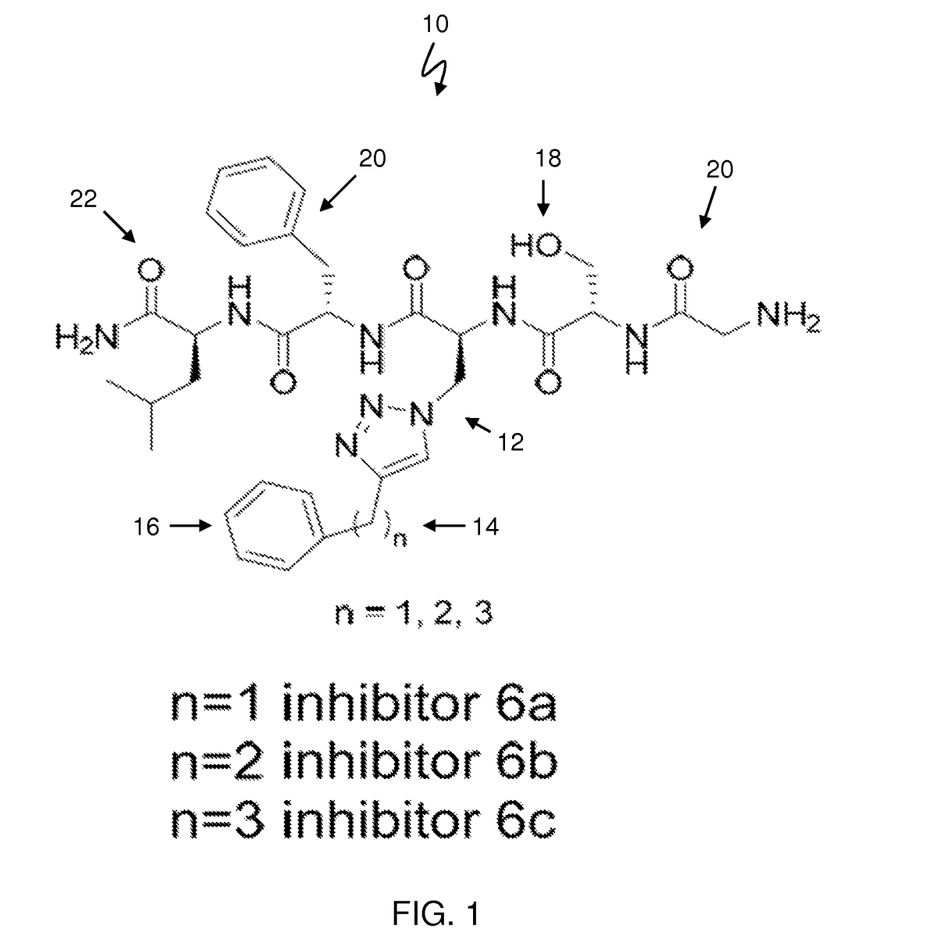
FIG. 1 is a chemical diagram of three exemplary synthetic grhelin O-acyltransferase inhibitors according to the present invention.

Referring now to the drawings, wherein like reference numerals refer to like parts throughout, there is seen in FIG. 1 a schematic representation of a grhelin O-acyltransferase inhibitor 10 according to the present invention. Inhibitors 10 generally comprise a triazole portion 12, an alkyl linker 14, and a hydrophobic aromatic group 16 on a side chain formed by linker 14. As seen in FIG. 1, the hydrophobic aromatic group may include various length linkers 14. Inhibitor 10 uses triazole portion 12 to incorporate aromatic and alkyl substituents, thereby mimicking the natural octanoyl group attached to ghrelin. As further seen in FIG. 1, inhibitors 10 may also include a serine residue 18 and a glycine residue 20 on one side of triazole portion 12, as well as a phenylalanine group 22 and a lipid moiety 24 on the other side of triazole portion 12.

Figure 2:
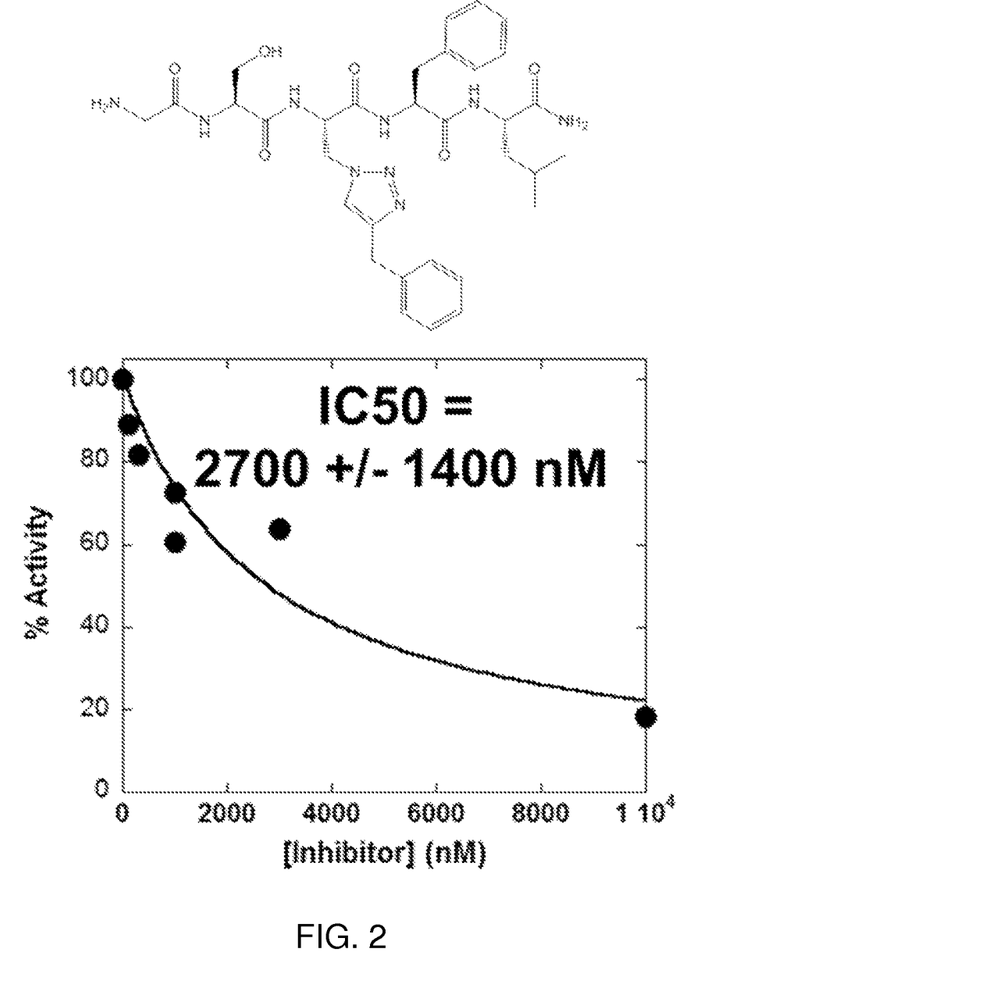
FIG. 2 is a graph showing efficacy testing of a first inhibitor incorporating a methylphenyltriazol hydrophic group according to the present invention.
Figure 3:
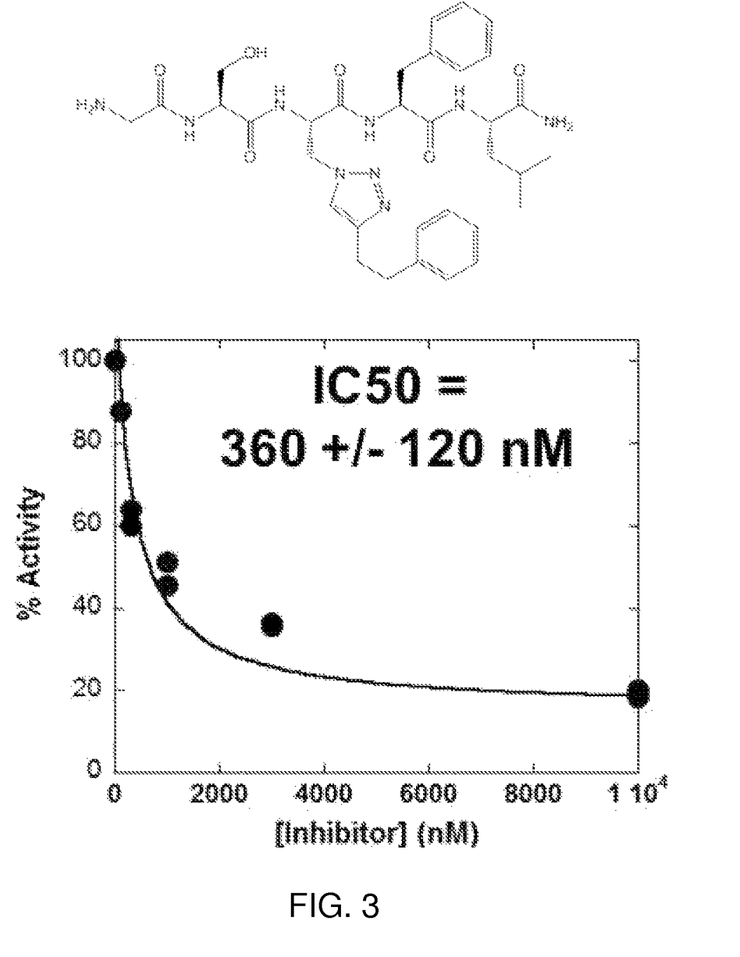
FIG. 3 is a graph showing efficacy testing of a second inhibitor incorporating a ethylphenyltriazole hydrophobic group according to the present invention.
Figure 4:
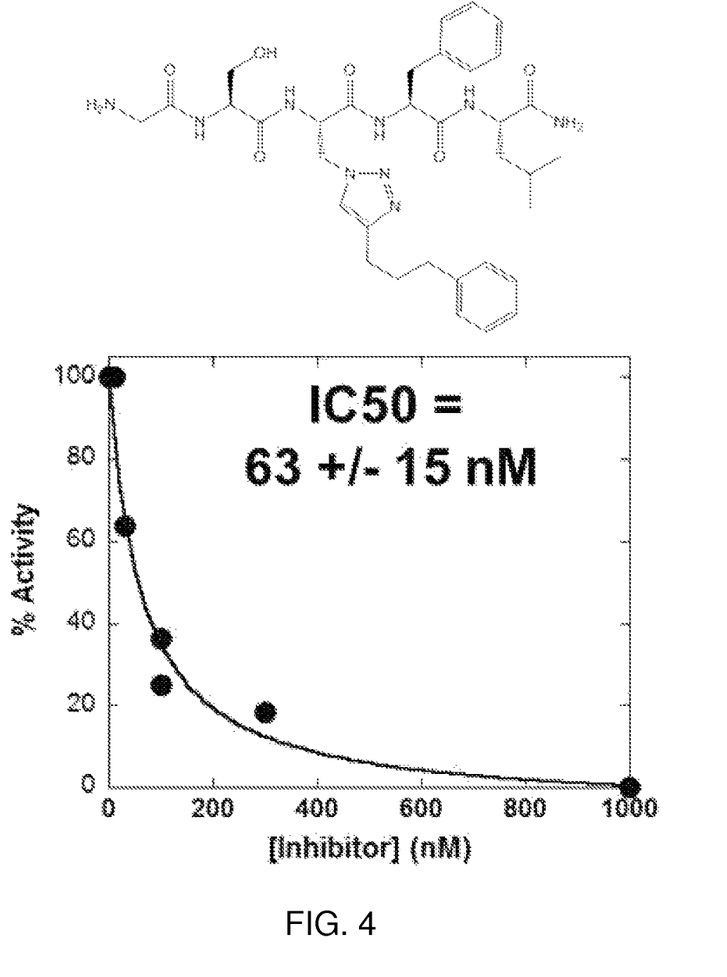
FIG. 4 is a graph showing efficacy testing of a third inhibitor incorporating a propylphenyltriazole hydrophobic group according to the present invention.

As seen in FIGS. 2-4, three grhelin O-acyltransferase inhibitors, n=1, n=2, and n=3 respectively, were synthesized and tested for activity using a fluorescence-based in vitro assay for grhelin O-acyltransferase inhibition. The fluorescence-based in vitro assay may comprise a ghrelin mimic peptide with a covalently attached fluorophore to serve as a fluorescent substrate, such as that discloses in U.S. application Ser. No. 14/046,131, hereby incorporated by reference in its entirety. More particularly, a peptide substrate derived from the N-terminal sequence of ghrelin that is labelled with a covalently attached fluorophore, such as the dansyl and acrylodan fluorophores, can serve as fluorescent substrate for evaluation of inhibitors 10 according to the present invention.

Figure 5:
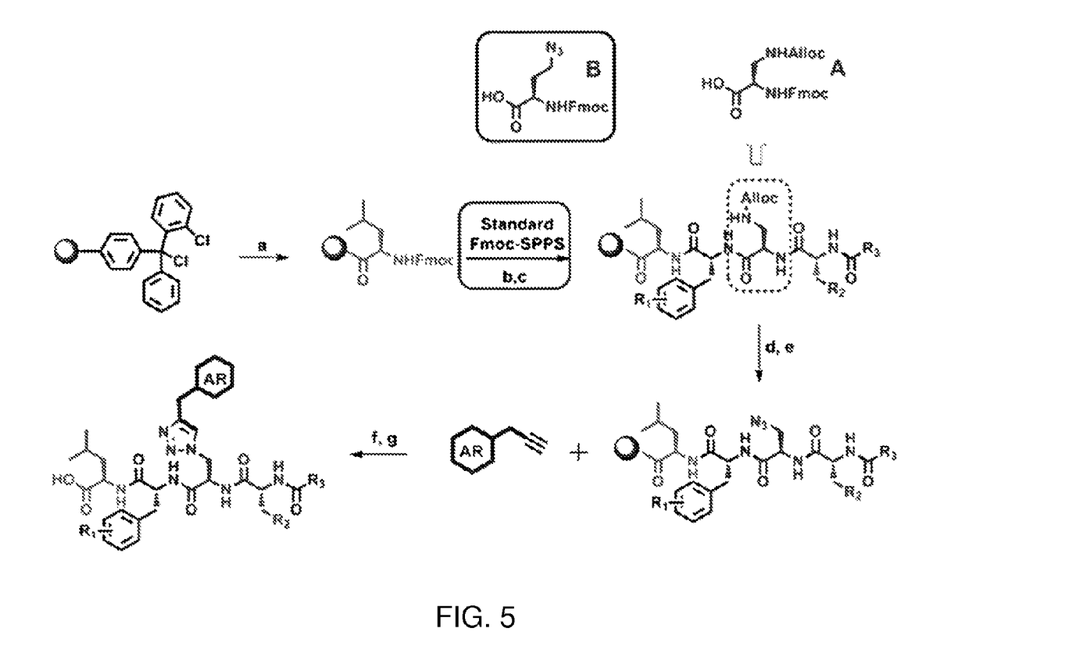
FIG. 5 is a schematic of the synthesis of synthetic grhelin O-acyltransferase inhibitors according to the present invention.

The synthetic route for ghrelin inhibitors may be seen in FIG. 5. Synthesis begins with the attachment of Fmoc-Leu to a chlorotrityl resin. Standard solid phase methods are then used to introduce a differentially protected amino acid A, followed by serine and glycine analogs. To introduce a different triazole placement into the peptide, the azido-substituted amino acid B could also be employed as an alternative. On resin click chemistry is then be used to introduce a lipid mimic as an alkyne, followed by the use of mild acidic conditions to release the candidate inhibitor from the resin. The inhibitors are then be HPLC purified and evaluated using the fluorescence-based assay discussed above.

Figure 6:
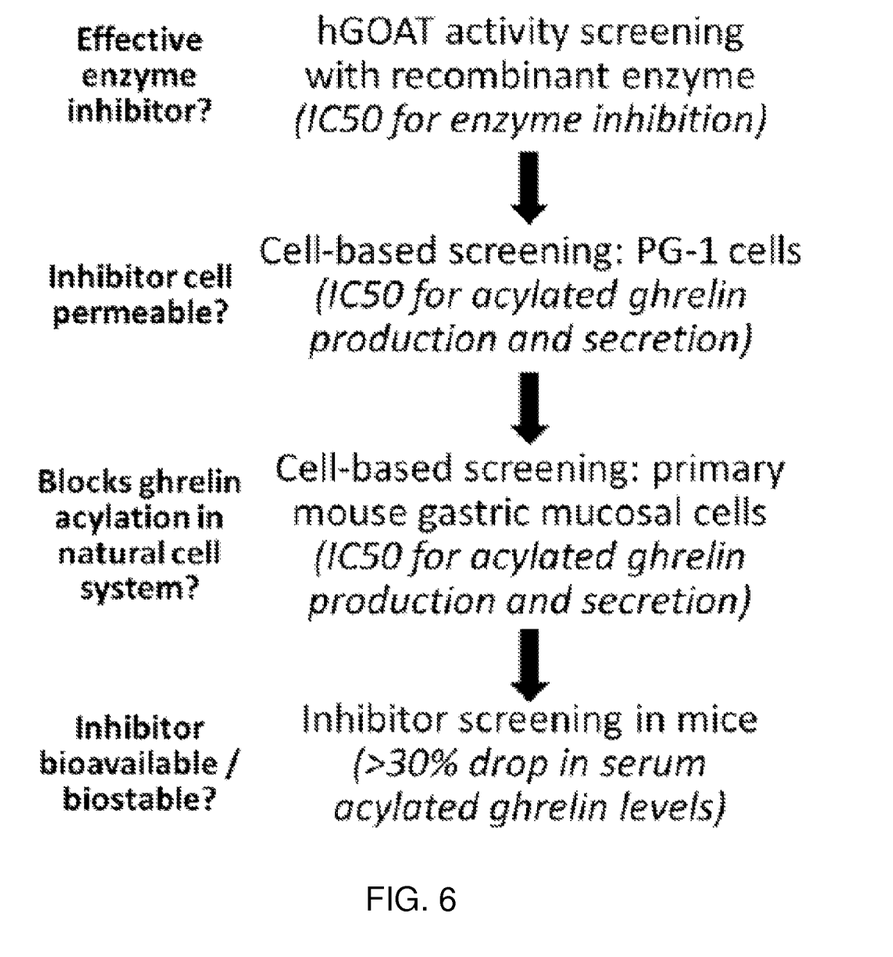
FIG. 6 is a flowchart of a protocol for establishing efficacy of synthetic grhelin O-acyltransferase inhibitors according to the present invention.

Inhibitors 10 according to the present invention may be further screened according to the protocol seen in FIG. 6. For ghrelin signaling (and, by extension GOAT inhibition) to be a reasonable pharmacological target for treating type II diabetes, two major requirements must be met. First, serum acylated ghrelin levels must be shown to modulate insulin secretion and sensitivity. Second, serum levels of acylated ghrelin must be sensitive to systemic treatment with a GOAT inhibitor. A growing number of studies implicate ghrelin, and more specifically the serum ratio of ghrelin to desacyl ghrelin, in the control of glucose homeostasis through insulin-related signaling. Studies in rodent models support that administration of ghrelin alone generally inhibits insulin secretion. A smaller number of studies in humans show that ghrelin can both lower fasting insulin levels and block glucose-stimulated insulin secretion by reducing insulin sensitivity. However, treatment with des-acyl ghrelin blocks the inhibitory effect of ghrelin on insulin secretion in cultured rodent islets, and co-injection of ghrelin and des-acyl ghrelin in both rodents and humans antagonizes the effects of either form of ghrelin alone on insulin secretion and blood glucose. This suggests the ratio of ghrelin to des-acyl ghrelin is a key regulatory parameter for controlling glucose homeostasis, consistent with evidence that ghrelin and des-acyl ghrelin concentrations are independently regulated. Clinical studies also support a connection between the serum ghrelin/des-acyl ghrelin ratio and insulin resistance/sensitivity. In human studies to date, this ratio has been altered by administering exogenous ghrelin and/or des-acyl ghrelin, raising the concern whether physiological levels of these hormones exert the same effects as pharmacological concentrations. Removal of stomach tissue through bariatric surgery has been shown to reduce serum ghrelin levels in some cases, but the suitability of surgical approaches for treating diabetes remains a topic of significant debate. As GOAT converts des-acyl ghrelin into ghrelin, inhibiting GOAT directly will alter the ghrelin/des-acyl ghrelin ratio without necessarily elevating the serum concentration of total ghrelin or incurring the risks of surgery.

To determine the ability of inhibitors 10 to block ghrelin signaling in these cells, $IC_{50}$ values may be determined using isolated primary mouse gastric mucosal cells. Mouse stomach tissue cells may be isolated and cultured, and ghrelin secretion can be assayed using commercially available ELISA kits. For these assays, mouse gastric mucosal cells may be isolated and cultured from mouse stomach tissue in a BSL-2 tissue culture facility using the published protocols. Tissue for these experiments may be collected from CD1 outbred mice. Inhibitor screening against primary mouse gastric mucosal cells may be performed by screening against PG-1 cells for dose dependence, time dependence, and cell viability. A threshold IC50 value for advancing inhibitors may be determined using $IC_{50}$ values for known hGOAT inhibitors, such as the GO-CoA-Tat and GS(octanoyl-Dap) FL inhibitors, with an initial $IC_{50}$ threshold set within five-fold of the GO-CoA-Tat inhibitor.

Inhibitors 10 may also be assayed for their ability to suppress acyl ghrelin levels in mice using established protocols for determining serum acyl ghrelin and total ghrelin levels in fasting mice. All studies will involve a sufficient numbers of animals (n=5-8/dose) to permit analysis of reproducibility and significance. In addition, a time course for serum ghrelin levels in fasting C57BL/6 mice may be used to determine the optimum fasting time for inhibitor screening. For example, it has been reported in the field that a 3-4-fold increase in plasma ghrelin levels follows a 24-hour fast.

Upon determining the optimal fasting time for enhancement of plasma ghrelin levels, a dose-response curve may be generated with inhibitors 10 to assess inhibition of acylated ghrelin secretion. Inhibitor efficacy may be analyzed (e.g. 0.1-40 mg/kg) via intraperitoneal (IP) administration one hour prior to initiation of fasting (e.g., 9 am inhibitor administration, 10 am-10 am fasting period). During the fasting period, blood samples will be collected from the retro-orbital sinus/tail vein in a time dependent manner (e.g., 0, 6, 12, 24 hours post drug administration) and plasma concentrations of acylated ghrelin and total ghrelin will be determined using commercial ELISA kits per manufacturer protocols. Inhibitors 10 demonstrating performance comparable to the previously reported GO-CoA-Tat inhibitor (Effective concentrations <40 mg/kg,>30% reduction in serum acyl ghrelin levels) will be considered good candidates for further investigation of effects on insulin signaling and glucose homeostasis.

What is claimed is:
1. A ghrelin O-acyltransferase inhibitor having a structure selected from the group consisting of

2. A method of inhibiting ghrelin O-acyltransferase, comprising the step of administering to a subject a ghrelin O-acyltransferase inhibitor having a structure selected from the group consisting of -continued and

* * * * *